United States Patent
Kolter et al.

(10) Patent No.: US 8,685,457 B2
(45) Date of Patent: *Apr. 1, 2014

(54) PHARMACEUTICAL FORMULATION FOR THE PRODUCTION OF RAPIDLY DISINTEGRATING TABLETS

(75) Inventors: Karl Kolter, Limburgerhof (DE); Michael Schönherr, Frankenthal (DE); Silke Gebert, Grünstadt (DE); Kathrin Meyer-Böhm, Feucht (DE); Angelika Maschke, Regensburg (DE)

(73) Assignee: BASF SE (DE)

( * ) Notice: Subject to any disclaimer, the term of this patent is extended or adjusted under 35 U.S.C. 154(b) by 780 days.

This patent is subject to a terminal disclaimer.

(21) Appl. No.: 12/663,417

(22) PCT Filed: Jun. 2, 2008

(86) PCT No.: PCT/EP2008/056765
§ 371 (c)(1),
(2), (4) Date: Oct. 7, 2009

(87) PCT Pub. No.: WO2008/148733
PCT Pub. Date: Dec. 11, 2008

(65) Prior Publication Data
US 2010/0178306 A1    Jul. 15, 2010

(30) Foreign Application Priority Data
Jun. 6, 2007  (EP) ................................. 07109725

(51) Int. Cl.
*A61K 9/14* (2006.01)
*A61K 9/16* (2006.01)

(52) U.S. Cl.
USPC .......................................... 424/489; 424/490

(58) Field of Classification Search
USPC ................................ 424/489, 490
See application file for complete search history.

(56) References Cited

U.S. PATENT DOCUMENTS

| | | | |
|---|---|---|---|
| 2,702,264 A * | 2/1955 | Klaui | 424/482 |
| 4,533,562 A * | 8/1985 | Ikegami et al. | 427/2.18 |
| 4,950,484 A * | 8/1990 | Olthoff et al. | 424/464 |
| 6,274,727 B1 | 8/2001 | Maul et al. | |
| 6,696,085 B2 | 2/2004 | Rault et al. | |
| 6,740,339 B1 * | 5/2004 | Ohkouchi et al. | 424/464 |
| 8,425,935 B2 * | 4/2013 | Kolter et al. | 424/465 |
| 2002/0071864 A1 | 6/2002 | Kim et al. | |
| 2003/0118642 A1 * | 6/2003 | Norman et al. | 424/465 |
| 2004/0180961 A1 * | 9/2004 | Lee et al. | 514/567 |
| 2005/0244343 A1 | 11/2005 | Wihiam et al. | |
| 2005/0244492 A1 | 11/2005 | Mehra et al. | |
| 2008/0069875 A1 | 3/2008 | Kakiguchi et al. | |
| 2008/0299194 A1 | 12/2008 | Kolter et al. | |

FOREIGN PATENT DOCUMENTS

| | | | |
|---|---|---|---|
| AU | 2006328585 B2 * | 5/2012 | |
| CA | 2634357 A1 * | 6/2007 | |
| EP | 0839526 A2 | 5/1998 | |
| JP | 2004026521 A | 1/2004 | |
| JP | 2008512420 A | 4/2008 | |
| WO | WO-98/22094 A2 | 5/1998 | |
| WO | WO-03/041683 A2 | 5/2003 | |
| WO | WO-03/051338 A1 | 6/2003 | |
| WO | WO 2006097456 A1 * | 9/2006 | |
| WO | WO-2007/071581 A2 | 6/2007 | |
| WO | WO 2007071581 A2 * | 6/2007 | |

OTHER PUBLICATIONS

Rowe et al., Aspartame, Handbook of Pharmaceutical Excipients, Pharmaceutical Press, 4th Edition, 2003, 37-39.*
U.S. Appl. No. 12/663,427, filed Dec. 7, 2009, Karl Kolter et al.

* cited by examiner

*Primary Examiner* — Gigi Huang
(74) *Attorney, Agent, or Firm* — Novak Druce Connolly Bove + Quigg LLP

(57) ABSTRACT

Pharmaceutical formulation in the form of agglomerates comprising
A) an excipient content composed of
  a) 60-97% by weight of sugar or sugar alcohols,
  b) 1-25% by weight of a disintegrant, selected from the group consisting of croscarmellose, sodium carboxymethylstarch and L-hydroxypropoylcellulose,
  c) 1-15% by weight of water-insoluble, film-forming polymers
  d) 0-15% by weight of water-soluble polymers and
  e) 0-15% by weight of further pharmaceutically customary excipients the total of the components a) to e) being 100% by weight.

15 Claims, No Drawings

PHARMACEUTICAL FORMULATION FOR THE PRODUCTION OF RAPIDLY DISINTEGRATING TABLETS

CROSS-REFERENCE TO RELATED APPLICATIONS

This application is a national stage application (under 35 U.S.C. §371) of PCT/EP2008/056765, filed Jun. 2, 2008, which claims benefit of European application 07109725.7, filed Jun. 6, 2007.

BACKGROUND OF THE INVENTION

The present invention relates to pharmaceutical formulations in the form of agglomerates for the production of rapidly disintegrating tablets, comprising sugar or sugar alcohols, disintegrant and water-insoluble polymers.

Tablets which disintegrate rapidly in the mouth and/or dissolve rapidly are becoming increasingly important for the oral administration of medicinal substances. Such tablets must disintegrate within a short time, preferably within 30 seconds, in the oral cavity and have a pleasant taste and must not leave behind a gritty sensation. Furthermore they should be easy to produce, with direct tableting having considerable advantages over wet granulation, and should have high mechanical strength so that they withstand packaging procedures, transport and also pressing out from packaging without damage.

The products and processes described to date do not meet these requirements or do so only very inadequately.

Rapidly disintegrating tablets frequently consist of sugar and sugar alcohols, effervescent systems, microcrystalline cellulose and other water-insoluble fillers, calcium hydrogen phosphate, cellulose derivatives, cornstarch or polypeptides. Furthermore, water-soluble polymers, conventional disintegrants (crosslinked PVP, sodium and calcium salts of crosslinked carboxymethylcellulose, the sodium salt of carboxymethyl starch, low-substituted hydroxypropylcellulose L-HPC) and substantially inorganic water-insoluble constituents (silicas, silicates, inorganic pigments) are used. Furthermore, the tablets may also comprise surfactants.

WO 2003/051338 describes a directly tablettable and readily compressible excipient formulation which comprises mannitol and sorbitol. First, art excipient premix is prepared by dissolution of mannitol and sorbitol in water and subsequent spray drying (customary spray drying and SBD method). Mannitol may also be added to this coprocessed mixture. Tablets which additionally comprise disintegrant, glidant, pigment and an active ingredient are said to disintegrate within 60 seconds in the oral cavity.

US 2002/0071864 A1 describes a tablet which disintegrates within 60 seconds in the oral cavity and is mainly formulated from a physical mixture of spray-dried mannitol and a coarse-particle crosslinked polyvinylpyrrolidone and a limited selection of active ingredients. These tablets have a hardness of about 40 N and produce an unpleasant, gritty mouthfeel.

According to U.S. Pat. No. 6,696,085 B2 a methacrylic acid copolymer of type C is to be used as a disintegrant. The methacrylic acid copolymer of type C is a polymer which is resistant to gastric fluid and insoluble in the acidic pH range but water-soluble in the pH range of 7 as is present in the oral cavity. In addition to low hardness (<20 N), the tablets have high friability (>7%) and have a high proportion in the region of 15% by weight of a coarse-particle disintegrant. They consequently have low mechanical strength and, owing to the high proportion of coarse-particle disintegrant, produce an unpleasant, gritty mouthfeel.

EP 0839526 A2 describes a pharmaceutical dosage form consisting of an active ingredient, erythritol, crystalline cellulose and a disintegrant. Furthermore, mannitol is incorporated and crosslinked polyvinylpyrrolidone is used as a disintegrant, so that a physical mixture forms. The tablets are said to decompose within 60 seconds in the oral cavity.

The application JP 2004-265216 describes a tablet which disintegrates in the mouth within 60 seconds and consists of an active ingredient, a water-soluble polyvinyl alcohol/polyethylene glycol copolymer, sugar/sugar alcohol (mannitol) and disintegrant.

BRIEF SUMMARY OF THE INVENTION

It was an object of the present invention to provide tablets which disintegrate rapidly in the mouth, leave behind a pleasant mouthfeel and are mechanically very stable.

Accordingly, a pharmaceutical preparation for the production of tablets which disintegrate rapidly in the mouth was found, which consists of agglomerates comprising
 a) 60-97% by weight of at least one sugar or sugar alcohol or mixtures thereof,
 b) 1-25% by weight of a disintegrant selected from the group consisting of croscarmellose, crosslinked sodium carboxymethylstarch and L-hydroxypropylcellulose,
 c) 1-15% by weight of water-insoluble polymers,
 d) 0-15% by weight of water-soluble polymers, and
 e) 0-15% by weight of further pharmaceutically customary excipients,
the total of the components a) to e) being 100% by weight.

Furthermore, a process for the production of such agglomerates has been found.

Furthermore, tablets which disintegrate rapidly in the mouth and comprise such preparations were found. The tablets disintegrate in the mouth or in an aqueous medium within 40 seconds, preferably within 30 seconds, particularly preferably within 20 seconds. "The tablets exhibit a disintegration time of <60 seconds in phosphate buffer, pH 7.2, at 37° C. The disintegration time is determined in a disintegration tester complying with USP or Pharm. Eur."

DETAILED DESCRIPTION OF THE INVENTION

The pharmaceutical preparations comprise, as component a), from 60 to 97% by weight, preferably from 70 to 95% by weight, particularly preferably from 75 to 93% by weight, of a sugar, sugar alcohol or mixtures thereof. Suitable sugars or sugar alcohols are trehalose, mannitol, erythritol, isomalt, maltitol, lactitol, xylitol and sorbitol. The sugar or sugar alcohol components are preferably finely divided, with average particle sizes of from 5 to 100 μm. If desired, the particle sizes can be adjusted by grinding. Preferred particle sizes are from 30 to 50 μm. However, it may also be advisable to use particle sizes smaller than 30 μm. It may likewise be advisable to employ sugars or sugar alcohols which comprise mixtures of fractions differing in particle size, for example mixtures of 30 to 70% by weight of a particle size fraction having an average particle size of <30 μm and 30 to 70% by weight of a particle size fraction having an average particle size of 30 to 50 μm. Mannitol, erythritol or mixtures thereof are preferably employed.

Disintegrants in amounts of from 1 to 25% by weight, preferably 2 to 15% by weight, particularly preferably 3 to 10% by weight, are employed as component b). Such disintegrants are water-insoluble but non film-forming. Suitable disintegrants are croscarmellose, a crosslinked carboxymethylcellulose, croscarmellose also meaning according to the invention the sodium and calcium salts thereof. Furthermore, sodium carboxymethylstarch is suitable. Likewise suitable is L-hydroxypropylcellulose, preferably having 5 to 16% hydroxypropoxy groups.

Water-insoluble polymers in amounts of from 1 to 15% by weight, preferably from 1 to 10% by weight, are used as component c). These are polymers. Preferred polymers are those which are insoluble in the pH range from 1 to 14, i.e. have a water insolubility which is pH independent at every pH. However, polymers which are water-insoluble at any pH in the pH range from 6 to 14 are also suitable.

The polymers should be film-forming polymers. In this context, film-forming means that the polymers have a minimum film forming temperature of from −20 to +150° C., preferably from 0 to 100° C., in aqueous dispersion.

Suitable polymers are polyvinyl acetate, ethylcellulose, methyl methacrylate/ethyl acrylate copolymers, ethyl acrylate/methyl methacrylate/trimethylammoniumethyl methacrylate terpolymers. Butyl methacrylate/methyl methacrylate/dimethylaminoethyl methacrylate terpolymers.

The acrylate/methacrylate copolymers are described in more detail in the European Pharmacopoeia as Polyacrylate Dispersion 30%, in the USP as Ammonio Methacrylate Copolymer and in JPE as Aminoalkyl Methacrylate Copolymer E.

Polyvinyl acetate is used as preferred component c). This may be used as an aqueous dispersion having solids contents of from 10 to 45% by weight. In addition, a preferred polyvinyl acetate is one having a molecular weight of from 100 000 to 1 000 000 daltons, particularly preferably from 200 000 to 800 000 daltons.

Furthermore, the formulations may comprise water-soluble polymers in amounts of from 0 to 15% by weight as component d). Suitable water-soluble polymers are, for example, polyvinylpyrrolidones, vinylpyrrolidone/vinyl acetate copolymers, polyvinyl alcohols, polyvinyl alcohol/polyethylene glycol graft copolymers, polyethylene glycols, ethylene glycol/propylene glycol block copolymers, hydroxypropylmethylcellulose, hydroxypropylcellulose, hydroxyethylcellulose, carrageenans, pectins, xanthans and alginates.

If desired, taste and appearance of the tablets obtained from the formulations can be further improved by adding pharmaceutically customary excipients (components e)) in amounts of from 0 to 15% by weight, for example such as acidifiers, buffer substances, sweeteners, flavors, flavor enhancers and colorants. The following substances are particularly suitable here: citric acid, tartaric acid, ascorbic acid, sodium dihydrogen phosphate, cyclamate, saccharin sodium, aspartame, menthol, peppermint flavor, fruit flavors, vanilla flavor, glutamate, riboflavin, beta-carotene, water-soluble colorants and finely divided color lakes.

By adding thickeners, such as high molecular weight polysaccharides, the mouthfeel can be additionally improved by increasing the softness and the sensation of volume.

Furthermore, surfactants may also be added as components e). Suitable surfactants are, for example, sodium lauryl sulfate, dioctyl sulfosuccinate, alkoxylated sorbitan esters, such as polysorbate 80, polyalkoxylated derivatives of castor oil or hydrogenated castor oil, for example Cremophor® RH 40, alkoxylated fatty acids, alkoxylated hydroxyl fatty acids, alkoxylated fatty alcohols, alkali metal salts of fatty acids and lecithins.

Furthermore, finely divided pigments may also be added for further improvement of the disintegration, because they increase the internal interfaces and hence water can penetrate more rapidly into the tablet. These pigments, such as iron oxides, titanium dioxide, colloidal or precipitated silica, calcium carbonates or calcium phosphates, must of course be very finely divided since otherwise a grainy taste once again results.

The formulations according to the invention can be produced by agglomeration in mixers, fluidized-bed apparatuses or spray towers. Solid starting materials and granulating liquid are first mixed with one another and the moist mixed material is then dried. According to the present invention, the granulating liquid used is an aqueous dispersion of component c), of the water-insoluble polymer.

In fluidized-bed agglomeration, an aqueous dispersion of the water-insoluble polymer is sprayed onto a fluidized mixture of sugar or sugar alcohol and crosslinked PVP, resulting in the agglomeration of the fine particles. The inlet air temperatures are 30 to 100° C., and the outlet air temperatures are 20 to 70° C.

In production in spray towers, the so-called FSD or SBD technology (FSD: fluidized spray drying; SBD: spray bed drying) is preferably used. Here, a solution of the sugar or sugar alcohol in water is first spray-dried and the addition of crosslinked PVP and the spraying in of an aqueous dispersion of the water-insoluble polymer are effected in the lower part of the spray dryer or in a connected fluidized bed, with the result that the particles agglomerate. Fine particles can furthermore be blown again in front of the spray nozzle of the sugar or sugar alcohol solution and additionally agglomerated. A procedure starting from the crystalline form of the sugar or sugar alcohol is also possible in the spray tower, FSD or SBD. The crystalline sugar or sugar alcohol is added at the top of the spray tower or in the recycle stream of fine material. By spraying an aqueous dispersion of the water-insoluble polymer, this crystalline solid is agglomerated in the tower.

It may prove advantageous for the agglomeration process to carry out a multistage spray process. At the beginning, the spray rate is kept low in order to prevent over-moistening of the initially charged product and hence adhesion thereof. With increasing duration of the process, the spray rate can be increased and thus the tendency to agglomerate can be raised. It is also possible to adapt the inlet air flow rate and/or temperature in an appropriate manner during the process. Particularly during the drying phase, it is advantageous to reduce the inlet air flow rate and hence to prevent abrasion of the agglomerates due to a high mechanical stress.

The fineness of the spray droplet of the binder solution or dispersion (adjustable via the atomization gas pressure), the nozzle geometry and the distance from the nozzle to the product bed may be regarded as further adaptation parameters for the agglomerate size. The finer and more uniform the spraying, the finer and more uniform are the resulting agglomerates. The further away the nozzle is from the product bed, the poorer is the agglomeration behavior.

Furthermore, the agglomeration can also take place in a mixer by continuous aggregation with mixing. Such a continuous form of aggregation with mixing is the so-called "Schugi granulation". There, solid starting materials and the granulating liquid comprising the water-insoluble polymer are thoroughly mixed with one another in a continuously operating vertically arranged high-speed mixer (cf. also M. Bohnet, "Mechanische Verfahrenstechnik", Wiley VCH Verlag, Weinheim 2004, page 198 et seq.).

According to a particular embodiment, the crosslinked PVP is suspended in the aqueous dispersion of the water-insoluble polymer.

The agglomerates thus obtained have an average particle size of 100-600 µm, preferably 120-500 µm and particularly preferably 140-400 µm. The water-insoluble, film-forming polymer serves as an agglomerating agent for agglomerating the fine sugar or sugar alcohol crystals and the particles of disintegrant.

The formulations according to the invention can advantageously also be used for the production of tablets which are left to disintegrate in a glass of water prior to use. The production of tablets which are swallowed intact is of course also possible.

For the production of the tablets, the customary processes can be used, direct tableting and roll compacting having particular advantages. Owing to the particular properties of the formulations according to the invention, as a rule only active ingredient, formulation according to the invention and a lubricant are required. The tablet formulation is therefore very simple and very reproducible and the process is easy to validate.

The granules according to the invention are in principle suitable for processing with all active ingredients. The granules are especially suitable for the production of pharmaceutical forms having the dosage of the respective active ingredient stated below, it also being possible to use the active ingredient in taste-masked form:
Zolmitriptan 2.5 mg, rizatriptan 5 mg, diphenhydramine HCl (taste-masked) 20 mg, brompheniramine 5 mg, chlorpheniramine 5 mg, pseudoephedrine (taste-masked) 30 mg, paracetamol (taste-masked) 250 mg, ibuprofen (taste-masked) 200 mg, acetylsalicylic acid 250 mg (taste-masked), hyoscyamine sulfate 0.125 mg, mirtazapine 15 mg,
selegeline HCl 1.25 mg, ondansetron 4 mg, olanzapine 5 mg, clonazepam 1 mg, cetirizine hydrochloride 10 mg, desloratadine 5 mg, enalapril maleate 5 mg, domperidone maleate 10 mg, scopolamine 0.25 mg,
oxazepam 15 mg, lorazepam 2.5 mg, clozapine 25 mg, dihydroergotamine mesylate 5 mg,
nicergoline 5 mg, phloroglucinol 80 mg, metopimazine 7.5 mg, triazolam 0.5 mg, protizolam 0.5 mg,
tramadol 50 mg, zolpidem tartrate 5 mg, cisapride 5 mg, risperidone 2 mg,
azithromycin 100 mg (taste-masked), roxithromycin 50 mg (taste-masked), clarithromycin 125 mg (taste-masked), erythromycin estolate 250 mg (taste-masked), apomorphine 20 mg, fentanyl 0.6 mg.

Surprisingly, it was found that a water-insoluble film-forming polymer considerably accelerates the disintegration of tablets. This is all the more surprising since such polymers are as a rule used for the preparation of slow-release pharmaceutical forms which do not disintegrate within several hours. The disintegration times with the use of polyvinyl acetate as the water-insoluble polymer are considerably shorter than in the case of water-soluble polymers.

Furthermore, the formulations according to the invention have extremely good flowabilities and compressibilities, which lead to mechanically very stable tablets. The hardness of the tablets produced with the aid of the pharmaceutical formulations according to the invention is >50 N. Frequently, the hardnesses are above 80 N, even with the use of active ingredients which are difficult to compress. The friabilities are <0.2%. There is therefore no damage during customary tablet handling.

EXAMPLES

The agglomerates were produced in a fluidized bed (GPCG 3.1, Glatt) by a top-spray process: sugar alcohol and disintegrant (croscarmellose, crosslinked sodium carboxymethylstarch, L-hydroxypropylcellulose) were introduced and agglomerated with aqueous binder dispersion. The aqueous binder dispersion used was a commercially available polyvinyl acetate dispersion (Kollicoat® SR30D, from BASF AG). The L-hydroxypropylcellulose used was a type with a hydroxypropoxy content of 11%.

TABLE 1

Formulation composition in % by weight

|  | A | B | C | D | E |
|---|---|---|---|---|---|
| Mannitol ($d_{0.5}$: 36 µm) | 90 | 90 | 90 | 44 | 76 |
| Erythritol ($d_{0.5}$: 44 µm) |  |  |  | 44 |  |
| Sorbitol ($d_{0.5}$: 47 µm) |  |  |  |  | 11 |
| Croscarmellose Na | 5 |  |  |  | 4 |
| Croscarmellose Ca |  |  |  | 8 |  |
| Crosslinked sodium carboxymethylstarch |  | 5 |  |  | 3 |
| L-Hydroxypropylcellulose |  |  | 5 |  |  |
| Kollicoat SR30D (solid) | 5 | 5 | 5 | 4 | 6 |

The following production parameters were used in a two-stage agglomeration process in which a relatively low spray rate was chosen initially and then the spray rate was increased:
Batch size; 0.6 kg
Concentration of the binder dispersion: 10% by weight solid
Table 2: Conditions for Producing the Formulations

|  | A | B | C | D | E |
|---|---|---|---|---|---|
| Inlet air temperature [° C.] | 49 | 52 | 52 | 51 | 53 |
| Outlet air temperature [° C.] | 25 | 28 | 31 | 27 | 31 |
| Spray rate | 15 g/min (10 min)/ remainder 20 g/min | 15 g/min (10 min)/ remainder 20 g/min | 15 g/min (10 min)/ remainder 20 g/min | 15 g/min (10 min)/ remainder 20 g/min | 15 g/min (10 min)/ remainder 20 g/min |

The agglomerates produced in this way were mixed with 2.0% by weight lubricant (Mg stearate) based on the mixture to be compressed in the Turbula mixer and processed in a fully instrumented eccentric press (Korsch XP1) at 30 strokes/min to tablets.

For the tableting, the eccentric press was equipped with a 10 mm punch (biplanar, faceted) and the compressive force was adjusted such that tablets having a hardness of 40-60 N resulted.

The tablets were investigated for hardness (HT-TMB-CI-12 F tablet tester from Kraemer), disintegration time in phosphate buffer of pH 7.2 (ZT 74 disintegration tester, Erweka) and release rate in gastric fluid (release apparatus, Erweka).

TABLE 3

Tablet properties

| | Tableting data | Tablet parameters | |
|---|---|---|---|
| | Compressive force [kN] | Hardness [N] | Disintegration time [s] |
| A | 4.0 | 49 | 15 |
| B | 3.7 | 51 | 21 |

TABLE 3-continued

| | Tablet properties | |
|---|---|---|
| | Tableting data | Tablet parameters |
| | Compressive force [kN] | Hardness [N] | Disintegration time [s] |
| C | 3.8 | 40 | 53 |
| D | 5.3 | 52 | 38 |
| E | 4.6 | 51 | 32 |

We claim:

1. A pharmaceutical formulation in the form of agglomerates consisting of
   a) 60-97% by weight of a sugar or sugar alcohol,
   b) 1-25% by weight of a disintegrant selected from the group consisting of croscarmellose, sodium carboxymethylstarch and L-hydroxypropylcellulose,
   c) 1-15% by weight of a water-insoluble, film-forming polymer selected from the group consisting of polyvinyl acetate, ethylcellulose, methyl methacrylate/ethyl acrylate copolymers, ethyl acrylate/methyl methacrylate/trimethylammoniumethyl methacrylate terpolymers, butyl methacrylate/methyl methacrylate/dimethylaminoethyl methacrylate terpolymers,
   d) 0-15% by weight of a water-soluble polymer and
   e) 0-15% by weight of a pharmaceutical excipient which is citric acid, tartaric acid, sodium dihydrogen phosphate, cyclamate, saccharin sodium, aspartame, menthol, peppermint flavor, fruit flavors, vanilla flavor, glutamate, water-soluble colorants or finely divided color lakes, the total of the components a) to e) being 100% by weight; wherein the average particle size of the agglomerates is from 100 µm to 600 µm.

2. The formulation according to claim 1, wherein the sugar alcohol is mannitol or erythritol or mixtures thereof.

3. The formulation according to claim 1, consisting of a croscarmellose as sodium or calcium salt.

4. The formulation according to claim 1, wherein component b) is an L-hydroxypropylcellulose having 5 to 16% hydroxypropoxy groups.

5. The formulation according to claim 1, wherein the water-insoluble film-forming polymer is polyvinyl acetate.

6. The formulation according to claim 1, wherein the water-insoluble film-forming polymer is polyvinyl acetate and is employed in the form of an aqueous dispersion.

7. The formulation according to claim 1, wherein the water-soluble polymer is polyvinylpyrrolidone.

8. The formulation according to claim 1, consisting of agglomerates composed of
   a) 70-95% by weight of the sugar or sugar alcohol,
   b) 2-15% by weight of the disintegrant selected from the group consisting of croscarmellose, sodium carboxymethylstarch and L-hydroxypropylcellulose,
   c) 1-10% by weight of the water-insoluble, film-forming polymer,
   d) 0-2% by weight of a water-soluble polyvinylpyrrolidone, and
   e) 0-15% by weight of the pharmaceutical excipient which is citric acid, tartaric acid, sodium dihydrogen phosphate, cyclamate, saccharin sodium, aspartame, menthol, peppermint flavor, fruit flavors, vanilla flavor, glutamate, water-soluble colorants or finely divided color lakes.

9. The formulation according to claim 1, consisting of agglomerates composed of
   a) 75-95% by weight of mannitol or erythritol or a mixture thereof,
   b) 3-10% by weight of a disintegrant selected from the group consisting of croscarmellose, sodium carboxymethylstarch and L-hydroxypropylcellulose,
   c) 1-10% by weight of a polyvinyl acetate,
   d) 0-2% by weight of a water-soluble polyvinylpyrrolidone, and
   e) 0-15% by weight of a pharmaceutical excipient which is citric acid, tartaric acid, sodium dihydrogen phosphate, cyclamate, saccharin sodium, aspartame, menthol, peppermint flavor, fruit flavors, vanilla flavor, glutamate, water-soluble colorants or finely divided color lakes.

10. A tablet consisting of the pharmaceutical formulation according to claim 1, wherein the tablet has a disintegration time of less than 30 seconds in aqueous medium.

11. The tablet according to 10, wherein the tablet has a hardness greater than 50 N.

12. The tablet according to claim 10, wherein the pharmaceutical excipient is present.

13. A process for producing a pharmaceutical formulation according to claim 1, which comprises agglomerating said sugar or sugar alcohol particles and said disintegrant with an aqueous dispersion of the water-insoluble film forming polymer, wherein said sugar or sugar alcohol are finely divided particles.

14. The process according to claim 13, wherein the agglomeration takes place in a fluidized bed granulator, a mixer or a spray tower.

15. A pharmaceutical formulation in the form of agglomerates consisting of
   a) 60-97% by weight of a sugar or sugar alcohol,
   b) 1-25% by weight of a disintegrant selected from the group consisting of croscarmellose, sodium carboxymethylstarch and L-hydroxypropylcellulose,
   c) 1-15% by weight of polyvinyl acetate,
   d) 0-15% by weight of a water-soluble polymer, and
   e) 0 to 15% by weight of a pharmaceutical excipient which is citric acid, tartaric acid, ascorbic acid, sodium dihydrogen phosphate, cyclamate, saccharin sodium, aspartame, menthol, peppermint flavor, fruit flavors, vanilla flavor, glutamate, riboflavin, beta-carotene, water-soluble colorants or finely divided color lakes,
   the total of the components a) to e) being 100% by weight and wherein the average particle size of the agglomerates is from 100 µm to 600 µm.

* * * * *